United States Patent
Sun et al.

(10) Patent No.: US 8,425,744 B2
(45) Date of Patent: Apr. 23, 2013

(54) ION SENSING CIRCUIT

(75) Inventors: Tai-Ping Sun, Taoyuan County (TW); Chung-Yuan Chen, Tainan County (TW); Hsiu-Li Shieh, Taichung (TW); Tak-Shing Ching, Taichung (TW)

(73) Assignee: National Chi Nan University, Puli, Nantou (TW)

( * ) Notice: Subject to any disclaimer, the term of this patent is extended or adjusted under 35 U.S.C. 154(b) by 253 days.

(21) Appl. No.: 12/927,221

(22) Filed: Nov. 9, 2010

(65) Prior Publication Data

US 2011/0247932 A1 Oct. 13, 2011

(30) Foreign Application Priority Data

Apr. 13, 2010 (TW) ................. 99111407 A

(51) Int. Cl.
*G01N 27/333* (2006.01)
(52) U.S. Cl.
USPC ............................ 204/406; 204/416; 257/253
(58) Field of Classification Search .................. 257/253; 204/416–419, 406; 422/82.03
See application file for complete search history.

(56) References Cited

U.S. PATENT DOCUMENTS 4,716,448 A * 12/1987 Kelly ............................ 257/253
6,353,323 B1 * 3/2002 Fuggle ......................... 324/438

OTHER PUBLICATIONS

"Op-Amps as Comparators" by V. Ryan downloaded from http://www.technologystudent.com/elec1/opamp3.htm on Sep. 16, 2012.*

* cited by examiner

*Primary Examiner* — Alex Noguerola
(74) *Attorney, Agent, or Firm* — Harrington & Smith

(57) ABSTRACT

An ion sensing circuit includes an ion sensing element configured for exposure to an electrolytic solution and control of a sensing current through the ion sensing element according to an ion concentration of the electrolytic solution. The ion sensing circuit further includes a current-to-voltage converter coupled electrically to the ion sensing element for generating a converted voltage from the sensing current. The ion sensing circuit also includes a comparator coupled electrically to the current-to-voltage converter for comparing the converted voltage and a threshold voltage to form a comparison result. In addition, the ion sensing circuit includes a latch coupled electrically to the comparator and the current-to-voltage converter. The latch is configured for sampling the output of the comparator according to a clock signal to generate a digital signal used by the current-to-voltage converter for converting the sensing current to the converted voltage.

12 Claims, 5 Drawing Sheets

ION SENSING CIRCUIT

CROSS-REFERENCE TO RELATED APPLICATION

This application claims priority of Taiwanese Application No. 099111407, filed on Apr. 13, 2010.

BACKGROUND OF THE INVENTION

1. Field of the Invention

The invention relates to a circuit, and more particularly to an ion sensing circuit.

2. Description of the Related Art

An ion-sensitive field-effect transistor (abbreviated as ISFET) is made by removing metal from the gate of an ordinary Metal-Oxide-Semiconductor Field-Effect Transistor (abbreviated as MOSFET) to be exposed to a solution. When a reference voltage used as a direct current bias voltage is placed into the solution to cause an electrolytic change of the solution, the channel current of the ISFET varies according to the ion (such as H+) concentration in the solution. Because the ISFET includes electrodes and the field-effect transistor, the ISFET can be incorporated with other electronic components to fabricate an ion sensing circuit that may be applied to biological medicine, analysis of water quality, and pH detection of unknown solutions.

As shown in FIGS. 1 and 2, each of a first and second conventional ion sensing circuit adjusts a gate potential of an ion-sensitive field-effect transistor 100, 200 using an operational amplifier 103, 202 to perform ion detection. An analog filter and an analog-to-digital converter are then used to filter and convert the electric potential of the gate into a digital signal.

Both of the foregoing conventional ion sensing circuits require an extra analog filter and an extra analog-to-digital converter for filtering and converting voltage signals from the ion-sensitive field-effect transistors into digital signals. Accordingly, both conventional ion sensing circuits may incur added design costs and increased circuit assembly complexity. In addition, for purposes of reducing noise, the conventional ion sensing circuits may include additional increased design complexity with respect to the operational amplifiers.

SUMMARY OF THE INVENTION

Therefore, the object of the present invention is to provide an ion sensing circuit that includes a simplified design and overcomes the disadvantages of the prior art.

Accordingly, an ion sensing circuit includes an ion sensing element configured for exposure to an electrolytic solution and control of a sensing current through the ion sensing element according to an ion concentration of the electrolytic solution. The ion sensing circuit further includes a current-to-voltage converter coupled electrically to the ion sensing element for generating a converted voltage from the sensing current. The ion sensing circuit also includes a comparator coupled electrically to the current-to-voltage converter for comparing the converted voltage and a threshold voltage to form a comparison result. In addition, the ion sensing circuit includes a latch coupled electrically to the comparator and the current-to-voltage converter. The latch is configured for sampling the output of the comparator according to a clock signal to generate a digital signal. The digital signal is used by the current-to-voltage converter for converting the sensing current to the converted voltage.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
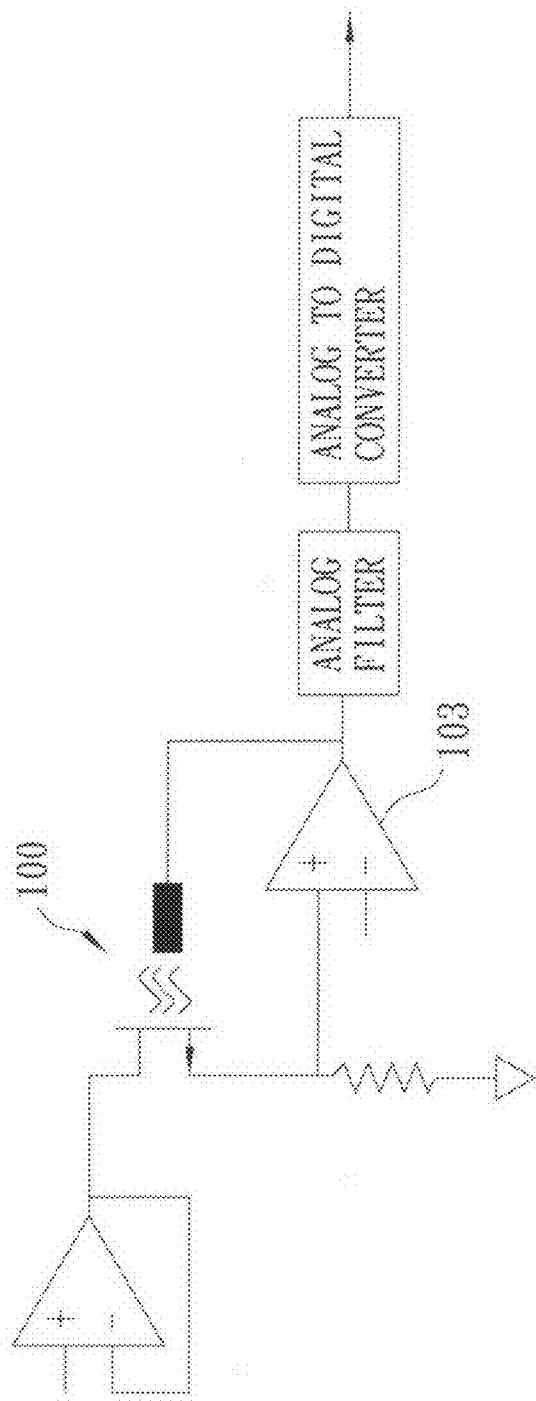
FIG. 1 is a circuit diagram of a conventional ion sensing circuit.
Figure 2:
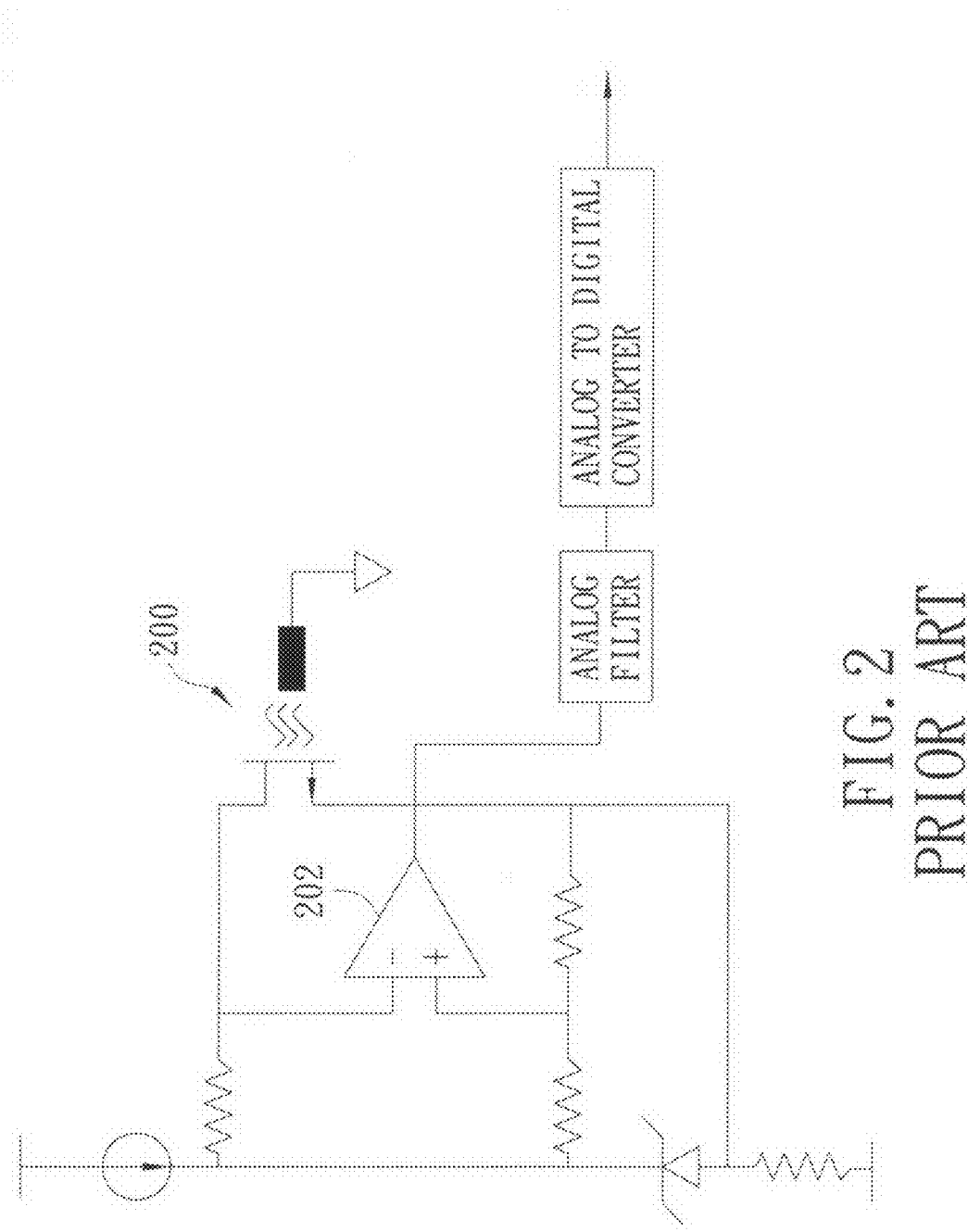
FIG. 2 is a circuit diagram of another conventional ion sensing circuit.

Before the present invention is described in greater detail with reference to the accompanying preferred embodiments, it should be noted herein that like elements are denoted by the same reference numerals throughout the disclosure.

Figure 3:
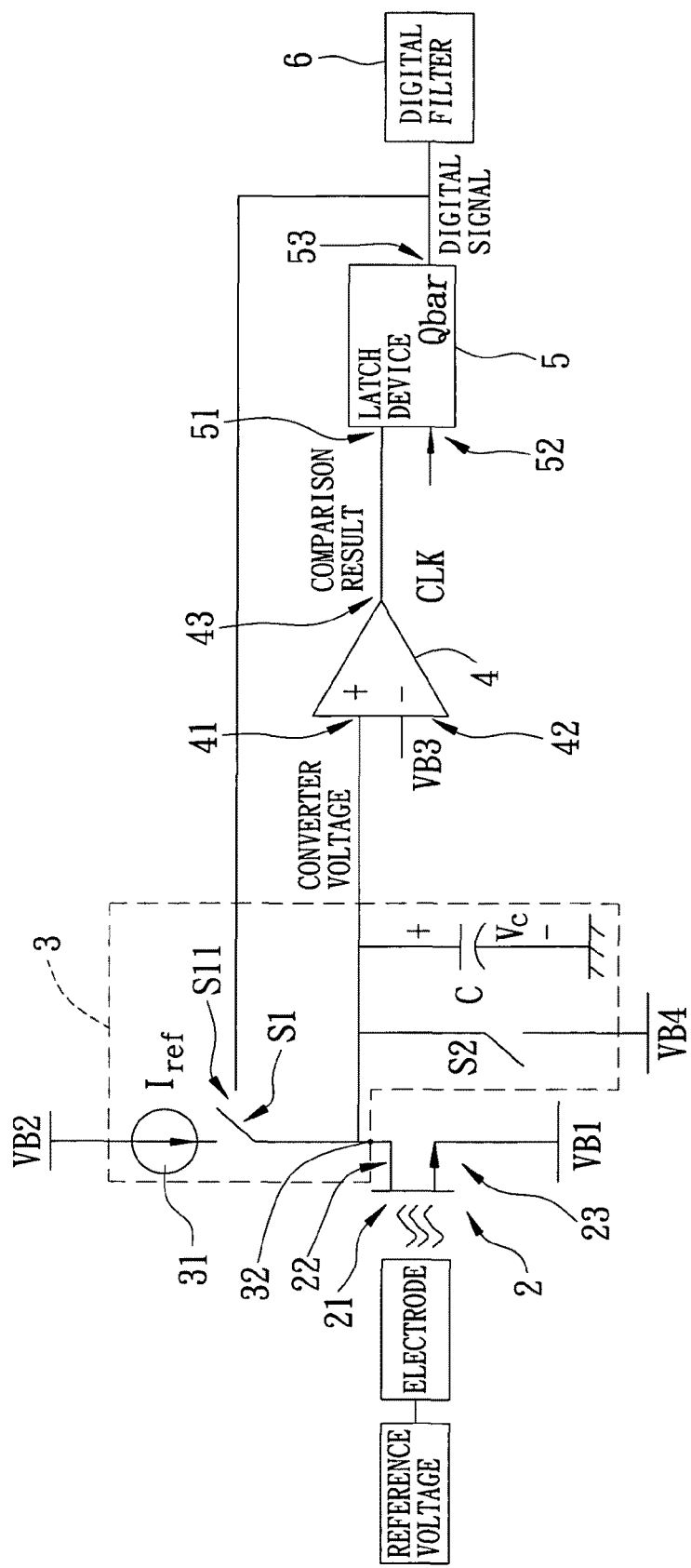
FIG. 3 is a circuit diagram of the first preferred embodiment of an ion sensing circuit according to the present invention.

Referring to FIG. 3, the first preferred embodiment of an ion sensing circuit according to the present invention is configured for detecting an ion concentration of an electrolytic solution for generating a related digital signal. The first preferred embodiment includes an ion sensing component 2, a current-to-voltage converter 3, a comparator 4, a latch device 5, and a digital filter 6.

The ion sensing component 2 is configured for exposure to an electrolytic solution, which causes it to generate a sensing current based on the ion concentration of the electrolytic solution, and includes a first end 21 for receiving a reference voltage, a second end 22 for outputting the sensing current related to the ion concentration of the electrolytic solution, and a third end 23 coupled electrically to a first electric potential (VB1).

In this embodiment, the ion sensing component 2 is an N-type ion-sensitive field-effect transistor. The first end 21 is the gate, the second end 22 is the drain, and the third end 23 is the source.

The current-to-voltage converter 3 is coupled electrically to the second end 22 of the ion sensing component 2 at a node 32 for receiving the sensing current. The current-to-voltage converter 3 provides a converted voltage (Vc) that relates to the ion concentration of the electrolytic solution in accordance with the sensing current. The current-to-voltage converter 3 includes a capacitor (C), a current source 31, and a first switch (S1).

The capacitor (C) is coupled electrically to a point between a ground potential and the second end 22 of the ion sensing component 2 for providing the converted voltage (Vc).

The current source 31 and the first switch (S1) are connected in series and coupled electrically between the second end 22 of the ion sensing component 2 and a second electric potential (VB2). The current source 31 is used for providing a reference current (Iref). The first switch (S1) includes a control end (S11) for controlling whether the first switch (S1) is at a conducting or non-conducting state to respectively permit or prevent current flow through the first switch (S1). When the first switch (S1) is at a conducting state and permits current flow, the reference current (Iref) increases the converted voltage (Vc).

The current-to-voltage converter 3 further includes a second switch (S2) coupled electrically between a fourth electric potential (VB4) and the second end 22 of the ion sensing component 2. The second switch (S2) may be controlled to switch between conducting and non-conducting states to respectively permit or prevent current flow through the second switch (S2). When the second switch (S2) is at a conducting state and current is permitted to flow through the second switch (S2), the converted voltage (Vc) is precharged to the fourth electric potential (VB4).

The comparator 4 includes a positive input end 41 coupled electrically to the current-to-voltage converter 3, a negative input end 42 for receiving a threshold voltage (VB3), and an output end 43 for providing a comparison result. When the comparator 4 receives the converted voltage (Vc) from the current-to-voltage converter 3, the comparator 4 generates a high or low electric potential comparison result according to the comparison between the converted voltage (Vc) and the threshold voltage (VB3). When the converted voltage (Vc) is higher than the threshold voltage (VB3), a high electric potential comparison result is output. Otherwise, a low electric potential comparison result is output.

The latch device 5 includes a data input end 51 for receiving the comparison result, a clock input end 52 for receiving a clock signal (CLK), and an output end 53 coupled electrically to the control end of the first switch (S1). In this embodiment, the output end 53 is an inverted output end (Qbar), and the first switch (S1) is an N-type transistor. The latch device 5 samples the comparison result according to the clock signal (CLK) to generate a digital signal. The digital signal is a reference based on the conversion of the sensing current (Iref) to the converted voltage (Vc). The digital signal is used to control operation of the first switch (S1).

In this embodiment, the first electric potential (VB1) is a low electric potential, and the second electric potential (VB2) and the fourth electric potential (VB4) are high electric potentials.

Figure 4:
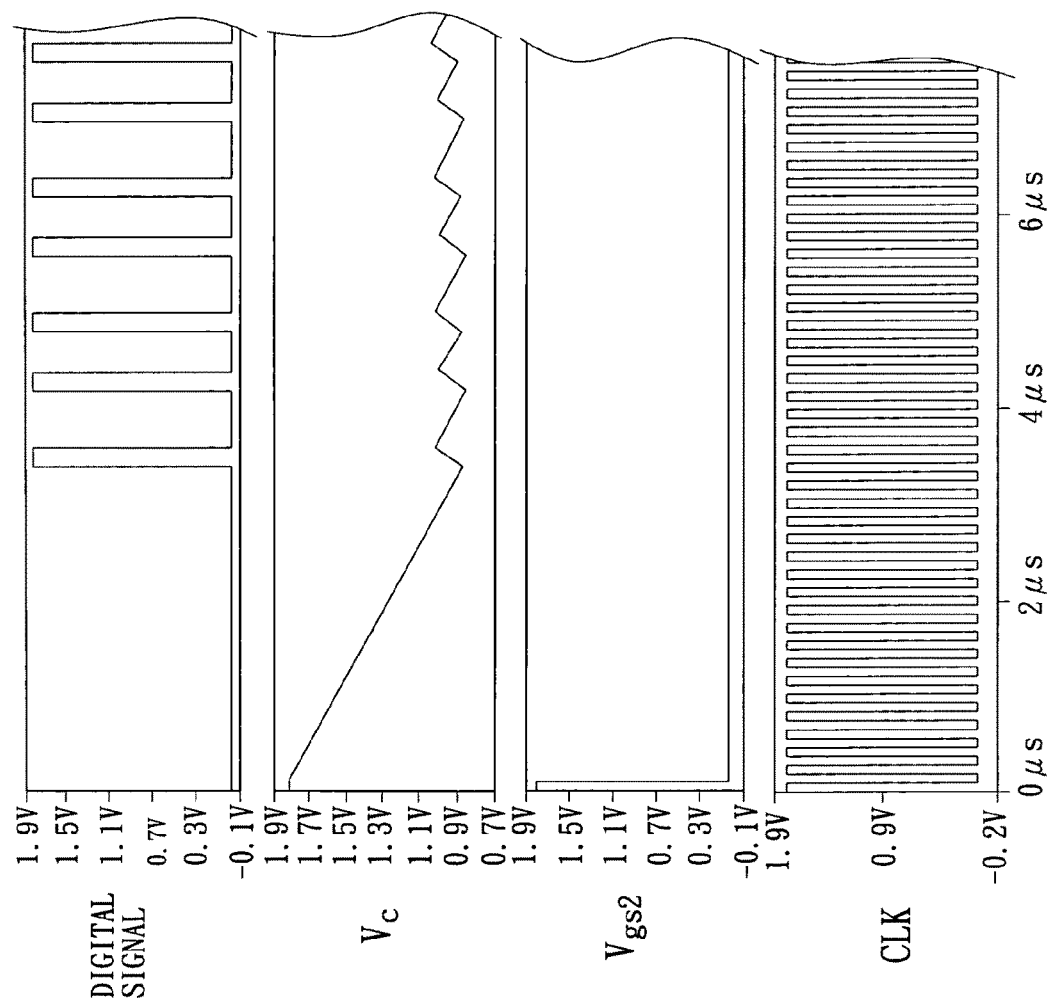
FIG. 4 is a simulated timing diagram of the first preferred embodiment.

As shown in FIG. 4, which is a simulated timing diagram of this invention, the electric potentials are defined as: VB1=0V, VB2=1.8V, VB3=0.9V and VB4=1.8V. However, in practice, the values of the electric potentials may be altered. The operation of the present embodiment is as follows:

Initially, a control signal (Vgs2) is generated to permit the second switch (S2) to conduct current for a predetermined time period while the current through the first switch (S1) is restricted, precharging the converted voltage (Vc) of the capacitor (C) to the fourth electric potential (VB4=1.8V). Next, current through the second switch (S2) is restricted, allowing the ion sensing component 2 to discharge the capacitor (C) according to the ion concentration of the electrolytic solution and generation of the sensing current. The converted voltage (Vc) gradually decreases until it reaches the threshold voltage (VB3=0.9V), which causes the output of the comparator 4 to change to a low potential.

The latch device 5 stores and converts the comparison result into digital signals according to the clock signal (CLK), the inverse phase output end (Qbar) outputs a digital signal with a logic value '1' to cause the first switch (S1) to change to the conducting state, so that part of the reference current (Iref) of the current source 31 charges the capacitor (C), and another part of the reference current (Iref) provides the sensing current of the ion sensing component 2 and raises the converted voltage (Vc) to the threshold voltage (VB3=09.V), changing the output of the comparator 4 to a high electric potential.

Afterwards, the latch device 5 stores and converts the output of the comparator 4 to a digital signal according to the clock signal (CLK). The inverted output Qbar outputs a logic '0' digital signal to stop current from flowing through the first switch 32. This allows the sensing current of the ion sensing element 2 to discharge the capacitor 34, which lowers the converted voltage (Vc). After the converted voltage (Vc) falls below the threshold voltage (VB3=0.9), the output of the comparator 4 becomes a low potential. The process is repeated to perform the process of sigma delta modulation.

The digital filter 6 is electrically coupled to the latch device 5 to gather digital signals over multiple clock signal (CLK) cycles to form a series signal that indicates the ion concentration. In this embodiment, the digital filter 6 is a counter that counts how many digital value '1's', or high potential signals, are in the multiple digital signals of the series signal. In addition, a duration of each digital signal is equal to one clock cycle.

Figure 5:
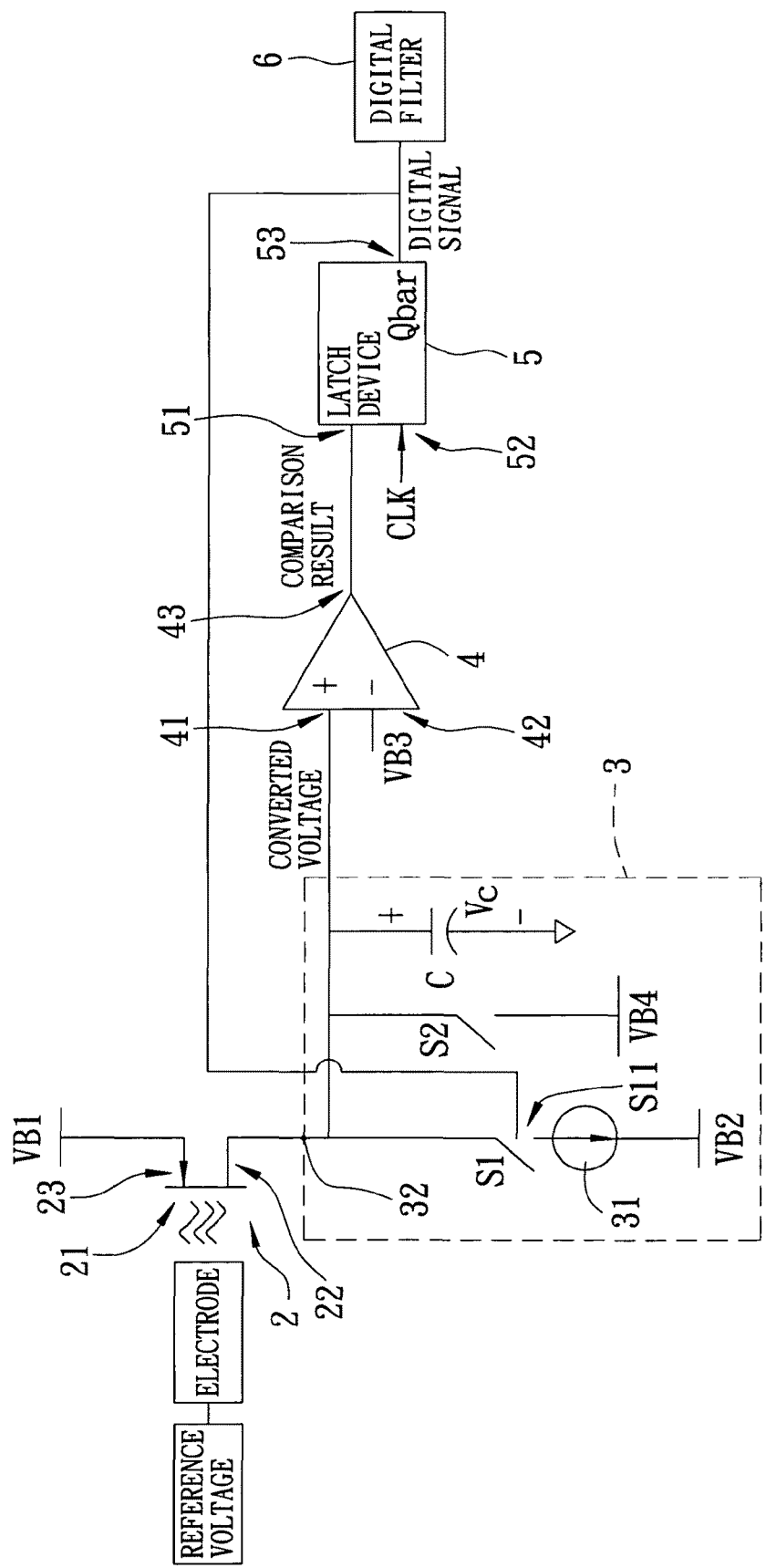
FIG. 5 is a circuit diagram of the second preferred embodiment of an ion sensing circuit according to the present invention.

Referring to FIG. 5, the second preferred embodiment of the ion sensing circuit according to this invention differs from the previous embodiment primarily in that the ion sensing component 2 is a P-type ion-sensitive field-effect transistor, the first electric potential (VB1) is a high electric potential, and the second electric potential (VB2) is a low electric potential. In the second preferred embodiment, the ion sensing component 2 charges the capacitor (C) according to the ion concentration of the electrolytic solution. Part of the reference current (Iref)) of the current source 31 discharges the capacitor (C), and another part of the reference current (Iref)) is made up of the sensing current of the ion sensing component 2. Other operations of the second preferred embodiment are similar to those of the first preferred embodiment, and hence are not further described.

In sum, this invention includes the following advantages:

1) The digital signals related to the ion concentration are directly output, making the analog filter and analog-to-digital converter unnecessary and saving the associated additional cost.

2) The output digital signals include more noise resisting capability than the prior art, and the design of the comparator 4 of the preferred embodiments is less complicated.

While the present invention has been described in connection with what are considered the most practical and preferred embodiments, it is understood that this invention is not limited to the disclosed embodiments but is intended to cover various arrangements included within the spirit and scope of the broadest interpretation to encompass all such modifications and equivalent arrangements.

What is claimed is:

1. An ion sensing circuit comprising:
an ion sensing element configured for exposure to an electrolytic solution and control of a sensing current through said ion sensing element according to an ion concentration of the electrolytic solution, said ion sensing element including an ion-sensitive field-effect transistor that comprises,
a first end for receiving a sensing voltage of the electrolytic solution that varies according to the ion concentration of the electrolytic solution,
a second end electrically coupled to a current-to-voltage converter, and
a third end, said second and third ends being configured to permit the sensing current to flow through the ion sensitive field-effect transistor according to the sensing voltage;
said current-to-voltage converter coupled electrically to said ion sensing element for generating a converted voltage from the sensing current, and including a capacitor coupled electrically between the second end of said ion sensing element and a ground potential, said capacitor being configured for providing the converted voltage, a current source for providing a reference current, and a first switch connected in series with said current source and comprising a control terminal for receiving a digital signal to control said first switch between conducting and nonconducting states, the converted voltage being varied by the reference current when said first switch is at the conducting state;

a comparator coupled electrically to said current-to-voltage converter for comparing the converted voltage and a threshold voltage to form a comparison result; and a latch coupled electrically to said comparator and said current-to-voltage converter, said latch being configured for sampling the output of said comparator according to a clock signal to generate the digital signal, the digital signal being used by said current-to-voltage converter for converting the sensing current to the converted voltage.

2. The ion sensing circuit of claim 1, wherein said ion-sensitive field-effect transistor is an N-type field-effect transistor, said first end is a gate, said second end is a drain, and said third end is a source configured to be coupled electrically to a low electric potential.

3. The ion sensing circuit of claim 2, wherein said first switch is connected in series with said current source between said second end of said ion sensing element and a high electric potential, said converted voltage being increased by the reference current when said first switch is at the conducting state.

4. The ion sensing circuit of claim 3, wherein said capacitor dissipates charge through said ion sensing element when the reference current is restricted by the digital signal from flowing through said first switch.

5. The ion sensing circuit of claim 1, wherein said ion-sensitive field-effect transistor is a P-type field-effect transistor, said first end is a gate, said second end is a drain, and said third end is a source configured to be coupled electrically to a high electric potential.

6. The ion sensing circuit of claim 5, wherein said first switch is connected in series with said current source between said second end of said ion sensing element and a low electric potential, said converted voltage being decreased by the reference current when said first switch is at the conducting state.

7. The ion sensing circuit of claim 6, wherein said capacitor accumulates charge from said ion sensing element when the reference current is restricted by the digital signal from flowing through said first switch.

8. The ion sensing circuit of claim 1, wherein said current-to-voltage converter further includes a second switch connected between a high electric potential and said second end of said ion sensing element, said second switch being configured to control whether the converted voltage of said capacitor is pre-charged to the high electric potential.

9. The ion sensing circuit of claim 1, wherein said comparator includes:

a positive input terminal coupled electrically to said current-to-voltage converter;

a negative input terminal for receiving the threshold voltage; and an output terminal for providing the comparison result, wherein said comparator receives the converted voltage from said current-to-voltage converter and provides the comparison result at either a high electric potential or a low electric potential according to the comparison between the converted voltage and the threshold voltage.

10. The ion sensing circuit of claim 1, further comprising a digital filter coupled electrically to said latch device for receiving a plurality of the digital signals to indicate the ion concentration.

11. The ion sensing circuit of claim 10, wherein a duration of each digital signal is equal to one clock cycle.

12. The ion sensing circuit of claim 10, wherein said digital filter is a counter for counting high signals of the plurality of digital signals.

* * * * *